(12) United States Patent
Knight

(10) Patent No.: US 9,037,268 B2
(45) Date of Patent: May 19, 2015

(54) SKULL-FOCUSED RF-BASED STIMULATION APPARATUS, SYSTEM AND METHOD FOR TREATING PATIENTS WITH ALZHEIMER'S DISEASE OR OTHER DEMENTIA

(71) Applicant: Eric A. Knight, Unionville, CT (US)

(72) Inventor: Eric A. Knight, Unionville, CT (US)

(*) Notice: Subject to any disclaimer, the term of this patent is extended or adjusted under 35 U.S.C. 154(b) by 0 days.

(21) Appl. No.: 14/024,595

(22) Filed: Sep. 11, 2013

(65) Prior Publication Data

US 2014/0330353 A1    Nov. 6, 2014

Related U.S. Application Data

(60) Provisional application No. 61/819,502, filed on May 24, 2013.

(51) Int. Cl.
| | | |
|---|---|---|
| *A61N 1/06* | (2006.01) | |
| *A61N 1/05* | (2006.01) | |
| *A61N 5/00* | (2006.01) | |
| *A61N 1/372* | (2006.01) | |

(52) U.S. Cl.
CPC .............. *A61N 1/0529* (2013.01); *A61N 5/00* (2013.01); *A61N 1/0526* (2013.01); *A61N 1/37211* (2013.01)

(58) Field of Classification Search
CPC  A61N 1/0529;  A61N 1/0526;  A61N 1/37211
USPC .................................................. 607/139, 45
See application file for complete search history.

(56) References Cited

U.S. PATENT DOCUMENTS

| 2004/0138722 A1* | 7/2004 | Carroll et al. ................... 607/45 |
| 2011/0112602 A1* | 5/2011 | Lee et al. ......................... 607/45 |
| 2012/0042506 A1* | 2/2012 | Bonn ............................... 29/600 |

OTHER PUBLICATIONS

Arendash, Gary W. et al. Electromagnetic Field Protects against and Reverses Cognitive Impairment in Alzheimer's Disease Mice. Jul. 20, 2009. Journal of Alzheimer's Disease. ISSN:1387-2877.*
ISSN:1387-2877, Journal of Alzheimer's Disease, Electromagnetic Field Treatment Protects Against and Reverses Cognitive Impairment in Alzheimer's Disease Mice.

* cited by examiner

*Primary Examiner* — Christopher D Koharski
*Assistant Examiner* — Michael Carey
(74) *Attorney, Agent, or Firm* — Damian Wasserbauer, Esq.; Wasserbauer Law LLC

(57) ABSTRACT

The portable, wearable, proximal Alzheimer's disease treatment invention is based upon creating an RF field of particular frequencies and intensities that are applied to the patient's head. To accomplish the aforementioned disease treatment functionality, a system was invented comprising a network of antennas connected to an RF generator via a feedline connector. The invention also provides methods for using measurements to monitor and manage the effectiveness of an ongoing disease treatment regimen, and databases which contain information about measurements, variables, and their relationships to clinical outcome.

39 Claims, 4 Drawing Sheets

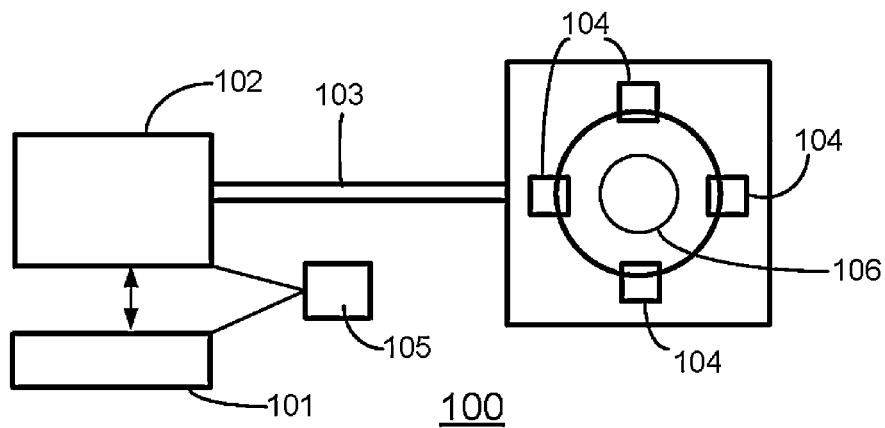
FIG. 1
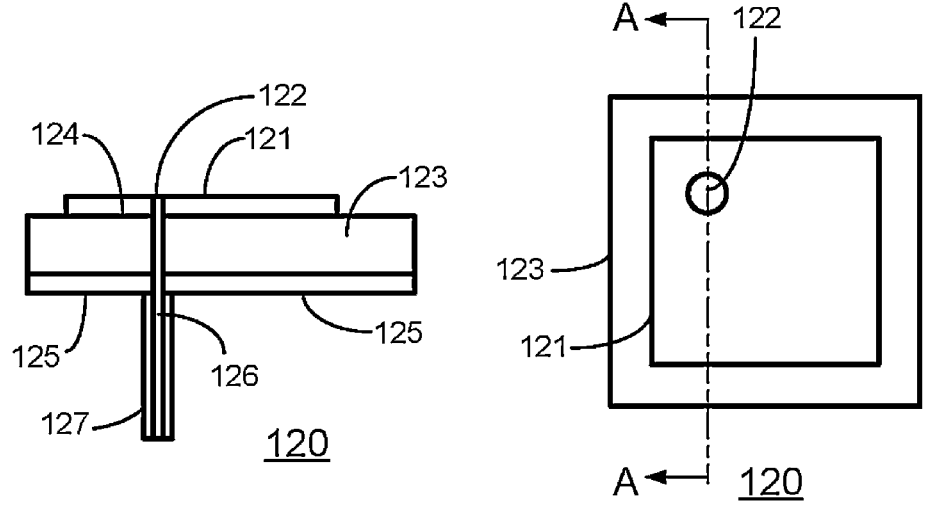
FIG. 2
FIG. 3

SKULL-FOCUSED RF-BASED STIMULATION APPARATUS, SYSTEM AND METHOD FOR TREATING PATIENTS WITH ALZHEIMER'S DISEASE OR OTHER DEMENTIA

The present invention claims benefit of U.S. provisional patent application No. 61/819,502 filed on May 5, 2013.

FIELD OF THE INVENTION

The present invention is an apparatus, system and method for applying radio-frequency stimulation to brain tissue of a patient to treat Alzheimer's disease, dementia, and other memory-loss indications uses at least one RF-based signal imparted directly to the cranium of the patient.

BACKGROUND OF THE INVENTION

Alzheimer's disease ("Alzheimer's"), dementia and other dementia-like symptoms are characterized by microscopic changes in the brain due to the destruction and death of nerve cells causing memory failure, personality changes, problems carrying out daily activities and other symptoms. The brain has approximately 100 billion nerve cells or neurons with each neuron connecting with many other neurons to form the communication network of the brain. In the context of memory, certain groups of nerve cells have the special function involved in thinking, learning and remembering. While it is not certain where such special-function nerve cells break down and become damaged, but as the damage spreads, these nerve cells lose their ability to do their function and eventually die, causing irreversible changes in the brain. Two abnormal structures called plaques and tangles are prime suspects in damaging and killing nerve cells.

The cause of Alzheimer's disease, dementia and other dementia-like symptoms cannot be determined in a number of patients; however, the most commonly accepted theory posits that it is the result of (1) plaque or deposits of a protein fragment called beta-amyloid that build up in the spaces between nerve cells an imbalance of certain chemicals in the brain, e.g., neurotransmitters; and (2) a protein tau that builds up inside cells and tangles nerve cells. Persons with Alzheimer's and other dementia have abnormal build up of these plaques and tangles. Scientists postulate that plaques and tangles play a critical role in blocking communication among nerve cells and disrupting the processes nerve cells need to survive. The effects include the destruction and death of nerve cells resulting in memory failure, personality changes, problems carrying out daily activities, and other symptoms of Alzheimer's, dementia, and other dementia-like conditions.

There is currently no effective treatment for Alzheimer's disease. It is estimated that 5.2 million Americans of all ages have Alzheimer's disease in 2013 including an estimated 5 million people age 65 and older and approximately 200,000 individuals younger than age 65 who have younger-onset Alzheimer's. By 2025 it is estimated that the number of people age 65 and older with Alzheimer's will increase 40 percent to 7.1 million, and by 2050, may triple to a projected 13.8 million. As a result, there is a need for an apparatus, system and method to prevent, slow, stop, or even cure Alzheimer's disease.

Moreover, it is estimated that the direct costs of caring for those with Alzheimer's to Americans with the disease will reach $203 billion, including $142 billion in costs to Medicare and Medicaid. Additional projections of total payments for health care, long-term care and hospice for people with Alzheimer's (and other dementias) are projected to increase from $203 billion in 2013 to $1.2 trillion in 2050 (in current dollars), representing a 500% increase in combined Medicare and Medicaid spending. As a result of the increase cost there is a need for an apparatus, system and method to prevent, slow, stop, or even cure Alzheimer's disease.

A drug-free approach, or complementing treatment, would be advantageous, as it would avoid the drug interactions and drug sensitivities common in the treatment of many illnesses. A small, portable system would have advantages over large facility-based systems, such as in hospitals, so as to have widespread availability of the device, for example, available to remote areas, family practitioner, clinics, and the like. As a result, there is a long-felt need for a portable, wearable, proximal, substantially uniform RF-field based apparatus useful to treat Alzheimer's disease that overcomes the problems of the prior art.

What is desired, then, is an apparatus, system and method to apply a substantially uniform RF field in a portable, wearable, proximal device to treat Alzheimer's disease with advantages of low cost, effective, efficient, durable and resilient to failure.

SUMMARY OF THE INVENTION

It is an object of the present invention to provide an apparatus, system and method of treatment of Alzheimer's disease, dementia, and other memory-loss disorders having at least one antenna appropriately sized and configured to be in close proximity to a patient's head, said antenna is optimized for the radio frequency selected for method of treatment, and said antenna connected to a radio-frequency generator through a radio-frequency transmission line connection.

It is an object of the present invention to provide an apparatus, system and method of treatment of Alzheimer's disease that is: portable, wearable, proximal to the patient, easy to use, and painless.

It is an object of the present invention to provide advantages of the apparatus, system and method of treatment that include little or no known side effects, a low manufacturing cost, a low cost of use, and operability via battery (for portable use) or suitable power source.

It is an object of the present invention to provide an apparatus, system and method of treatment that advantageously can be operated in clinical, public, or personal environments, or offers treatment that can be administered by any clinician with minimal training, or offers treatment that can be self administered by the patient if the patient is in the early stages of the disease.

It is yet another object of the present invention to provide an apparatus, system and method of treatment that advantageously can be configured to provide either a symmetrical or focused therapeutic RF field about the patient's head; the lowest-intensity RF field strength to produce the necessary therapeutic benefit without adverse ionization affects; and, due to its designed proximity to the patient and its low-intensity RF field, (1) has a negligible effect on nearby non-patients and (2) has a negligible effect on nearby electronic devices, particularly important if the invention is used in a clinical environment containing sensitive electronic-based medical systems.

It is an object of the present invention to provide a method of treatment for Alzheimer's disease, dementia, and other memory-loss disorders that positions at least one RF antenna on or proximate to at least one of the patient's brain regions; and activates the at least one antenna, preferably a microstrip antenna unit, to apply a radio frequency (RF) signal to at least one of one of the brain's regions in a predetermined non-ionization RF frequency and intensity insufficient to ionize atoms or molecules of that comprise the brain. It is an object of the present invention to provide such a method of treatment in a software program to control the numerous parameters of the treatment including frequency, time, dosage, power, activating one or more antennae in an array and/or in a predetermined pattern.

It also is an object of the present invention to provide an apparatus adapted to a helmet to provide the method of treatment for Alzheimer's disease, dementia, and other memory-loss disorders to the patient in a portable, wearable device.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIG. 1 illustrates block diagram of the apparatus, system, and method in accordance with an embodiment of the present invention;

FIG. 2 illustrates a schematic side view of a microstrip RF antenna along lines A-A of FIG. 3 of the present invention;

FIG. 3 illustrates a schematic top view of a microstrip RF antenna of the present invention;

DESCRIPTION OF THE EMBODIMENTS

Figure 4:
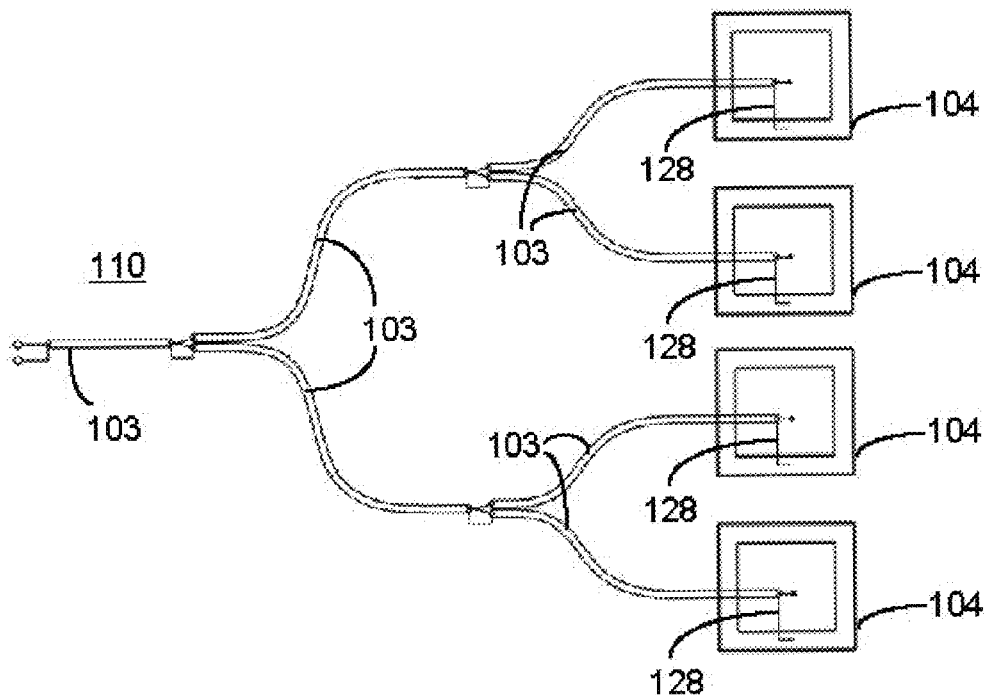
FIG. 4 illustrates a schematic of a cable-based power divider and antenna network in accordance with an embodiment of the present invention.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "stimulating" refers to causing a neuron or group of neurons or nerve cells in the brain such as phenopalatine ganglion ("SPG", also called the pterygopalatine ganglion), the sphenopalatine nerve ("SPN", also called the pterygopalatine nerve), the nerve of the pterygoid canal, also termed the vidian nerve ("VN"), autonomic ganglia and dorsal roots exiting the spine, and/or all other central and peripheral nerves and ganglia, for treatment in the head to suppress, prevent or cure a host of disorders including Alzheimer's disease, dementia and other dementia-like symptoms and neuropsychiatric related disorders in a mammal or human patient (hereinafter, referred to as a "patient") i.e., change a property of the neuron function. For example, the neuron could be affected in its transformation of information (e.g., homeostatic information transmission rates), or it could either quench (either reduce or stop activity altogether) or kindle (activate or increase in activity). Depending on the condition to be treated, one having ordinary skill in the relevant art will be able to determine if and/or how a particular neuron or brain region needs to be stimulated to achieve the desired treatment effect.

In some embodiments, the present invention relates to a method for treatment of Alzheimer's disease, dementia and other dementia-like symptoms or related neuropsychiatric-conditions by stimulating the patient's brain with an RF frequency between about 100 kHz and 300 GHz, including specifically 918 MHz.

It is to be appreciated that the frequency of 918 MHz is chosen as a point of interest as such frequency resulted in certain discoveries related to a cellular-level discovery by the Department of Cell Biology, Microbiology, and Molecular Biology of the University of South Florida (USF) as potentially representing a therapeutic agent against Alzheimer's disease in concert with finding that EMF exposure as a non-invasive, non-pharmacologic approach worthy of vigorous investigation. The apparatus, system and method for applying radio-frequency stimulation to brain tissue of a patient of the present invention is an application of the initial cellular-level discovery.

Accordingly, as can be understood by one having ordinary skill in the relevant art, stimulating the neurons of the human brain with the inventor's device is intended to stop or improve short-term memory decline; the ability to perform routine tasks; worsening judgment; neurological disorders including emotional outbursts; language impairment; changes in behavior, such as wandering and agitation; and other symptoms and manifestations of Alzheimer's disease, dementia and other dementia-like conditions. Medical conditions which may be treated by the present invention's systems and methods include, but are not limited to: Alzheimer's disease, dementia and other dementia-like symptoms or related neuropsychiatric disorders or a combination of the above.

Treatment of amyloid plaques by the present invention's systems and methods include plaque or deposits of a protein fragment called beta-amyloid that builds up in the spaces between nerve cells an imbalance of certain chemicals in the brain, e.g., neurotransmitters. Accordingly, as can be understood by one having ordinary skill in the relevant art, amyloid is a general term for protein fragments that the body produces normally and beta amyloid is a fragment of a protein snipped from another protein called amyloid precursor protein (APP), whereby, in a healthy brain, these protein fragments would break down and be eliminated. In Alzheimer's disease, the fragments accumulate to form hard, insoluble plaques. The method of treatment of amyloid plaque conditions include, but are not limited to: Alzheimer's disease, dementia and other dementia-like symptoms or related neuropsychiatric disorders or a combination of the above.

Treatment of neurofibrillary tangles by the present invention's systems and methods include treating insoluble twisted fibers found inside the brain's cells consisting primarily of a protein tau that builds up inside cells and tangles nerve cells. Accordingly, as can be understood by one having ordinary skill in the relevant art, the protein tau causes neurofibrillary tangles or insoluble twisted fibers found inside the brain's cells, which tangles consist primarily of the protein tau forming part of a structure called a microtubule and functions to transport nutrients and other important substances from one part of the nerve cell to another. In Alzheimer's disease, the tau protein is abnormal and the microtubule structures collapse. The method of treatment of neurofibrillary tangles conditions include, but are not limited to: Alzheimer's disease, dementia and other dementia-like symptoms or related neuropsychiatric disorders or a combination of the above.

In order to determine the amount of time to achieve the desired effect according to a method of treatment described herein, the effect is configured from a number of variables including a non-ionization RF frequency and intensity insufficient to ionize atoms or molecules of the brain as discussed in the present application. In some embodiments, a single treatment can be applied to a patient during a predetermined period of time. In alternate embodiments, multiple treatments each having a predetermined application time can be applied, where a total application time of all treatments can be predetermined as well. Treatments can also be repeated on an as needed basis depending, for example, on the severity and type of disorder being treated, and/or exact positioning in the patient. As can be understood by one having ordinary skill in the relevant art, times, frequencies, and intensities of treatment can be determined based on the patient (e.g., physical condition, characteristics, etc.), condition being treated, characteristics of the antennae source (e.g., wavelength, etc.), and/or any other factors.

The present invention provides an apparatus, system and methods for applying stimulation of a radio-frequency (RF) field between approximately 100 kHz and 300 GHz, and specifically 918 MHz with 0.25 W/kg brain-matter RF dosage, to one or more nerve cells or neurons via a "skull-mounted" or "head-mounted" or otherwise portable, wearable, and proximal RF-based apparatus fitted over or in close proximity to the human head. RF stimulation of neurons via the apparatus, system, and methods of the present invention can provide significant therapeutic benefit in the management of Alzheimer's disease, dementia and other dementia-like indications as detailed herein.

As is illustrated in FIGS. 1-10, one embodiment of the portable, wearable, proximal Alzheimer's disease treatment invention is described. Accordingly, the system 100 for the treatment is carried out by employing at least one controller 101, RF signal generator 102, connector or feed line 103, antennae 104 and a power source 105 for providing a treatment to a patient's head 106. The controller or control unit 101, in the context of the present invention, is a hardware device or a software program that controls, manages or directs the RF signal generator 102 on the signaling to apply to each or all of the at least one microstrip antennae 104. The system 100 includes a power source 105 for supplying energy to the electrical components of the system including, for example, the controller 101, the RF signal generator 102 and the antennae 104 via the connector 103. The power source 105 can be an AC-based power supply or, for portability, a battery that preferably has an extended the time between recharges such as, for example, a Lithium-ion battery system or battery pack.

In an embodiment where the controller 101 is a computer, the controller 101 preferably includes a programmable memory for storing data and/or control stimulation parameters to allow adjusting the RF signal produced by the RF signal generator 102 in frequency, pulse width, modulation, duration, and/or intensity. For example, the controller 101 may be a computer system that is programmed to operate the RF signal generator 102 and microstrip antennae 103 arranged as an array, network, or otherwise used for the desired method of treatment. The controller 101 is connected to a computer-readable storage medium that can store computer-executable process steps for implementing a method of treatment according to predetermined parameters and patterns. The computer-executable process steps can comprise a computer program that implements a method of treatment according to predetermined parameters and patterns of the present invention.

In each of these examples, the controller 101 can control parameters of frequency, pulse width, modulation, duration, and/or intensity and adjust to levels that are safe and efficacious to provide therapy to a patient. In this manner, the controller 101 can provide RF stimulation of neurons by creating an RF field of particular frequencies, durations, intensities, and other parameters that are applied to the patient's head 106. It is envisioned that most clinical requirements for treating Alzheimer's disease will require a substantially symmetrical, uniform RF field, and was thus the most tested and developed aspect of the present invention. However, it is a simple matter to bias the RF field, focusing the RF field to specific areas of the brain, and thus the scope of the present invention should be similarly comprehensive.

As is illustrated in FIG. 1, and according to an embodiment of the present invention, the signal generator 102 can be an RF generator manufactured by the Kenwood Corporation, model Kenwood TK-9401. The RF signal generator is 102 configured to provide a continuous RF carrier wave at a frequency of 918 MHz. In addition, the RF signal generator 102 can provide variable power output of between approximately 100 milliwatts to 10 watts so as to apply an appropriate RF "dosage." In this manner, the RF signal generator 102 can vary the power output such as, for example, 0.25 watts per kilogram of brain matter so that the appropriate RF dosage can be delivered—in a substantially uniform directional pattern—to the nerve cells or neurons of the brain of the patient. Alternatively, the signal generator 102 can be a lightweight, compact RF signal generator commercially available or, alternatively, specifically designed and manufactured according to the parameters of the present invention.

Figure 5:
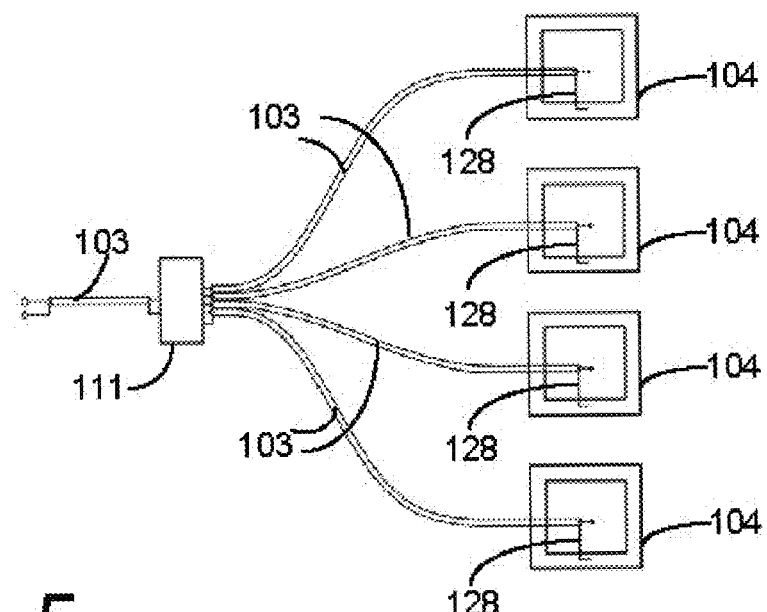
FIG. 5 illustrates a schematic diagram of a hardware-based power divider and antenna network of the present invention.
Figure 8:
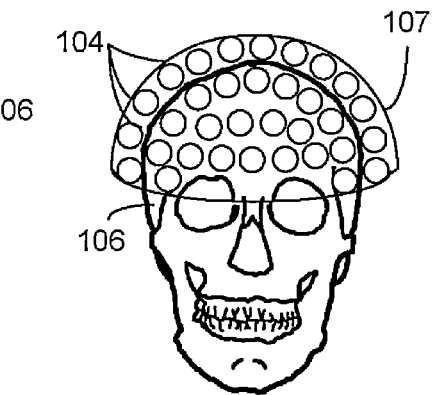
FIG. 8 illustrates a front view of a portable, wearable apparatus incorporating the microstrip RF antenna and a method of treatment according to the present invention.
Figure 9:
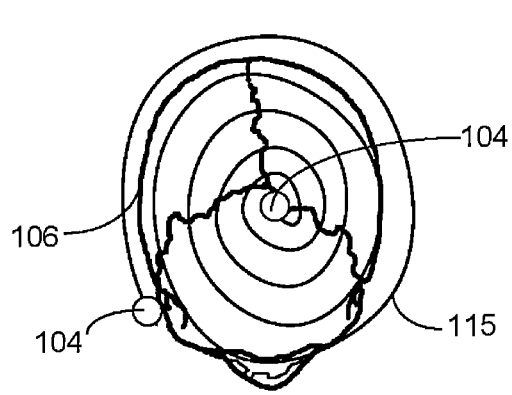
FIG. 9 illustrates a top view of the apparatus and a spiral treatment according to the method of the present invention.
Figure 10:
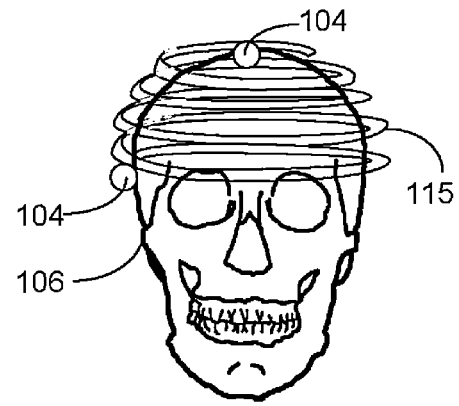
FIG. 10 illustrates a front view of the apparatus and a spiral treatment according to the method of the present invention.

As is illustrated in FIGS. 2 and 3, a microstrip RF antenna assembly 120 generally comprises a radiating element 121, an antenna feed point 122, a substrate 123, a radiating element 124, a ground plane element 125, a center conductor of radiating element feed line 126, an outer conductor of the feed line 127, and a substrate feed point 128 (as shown in FIGS. 4 and 5). The microstrip antennas 104 of the present invention can be constructed from RO3006® RT/duroid® ceramic-filled PTFE composite laminate, which are manufactured by the Rogers Corporation. The substrate 123 can be configured from PTFE composite laminate or other high-frequency-circuit-suitable antenna material substrates used to construct microstrip antennas, which should not limit the scope of the present invention. Alternatively, the microstrip antennae 104 including the radiating element 121 and substrate 123 can be configured to conform to the human head or inside of a helmet 107 as shown in FIG. 8.

In operation, a constant-carrier RF signal can be applied to the patient's 106 brain according to the present invention. Alternatively, all sorts of signal types including pulsed or modulated (amplitude or frequency) RF signals that accomplish the method of treatment and indicate clinical benefits can be used, whereby these various operating modes are thus intrinsically within the spirit and scope of the present invention.

As shown in FIGS. 4 and 5, the connector 103 of the present invention can be constructed of coaxial feed line, for example, RG-316 coax. Alternatively, the connector 103 can take-multi-connector form 110 to signal more than one microstrip antennae 104, for example, four microstrip RF antennas 104 in an array as shown in FIGS. 1, 4 and 5. In this embodiment, the system 100 is adapted to provide adjustments for the velocity factor of the cable. In FIG. 4, velocity factor adjustments are made whereby the middle cable sections are a quarter-wavelength long, for example, are approximately nine inches long so as to adjust for the velocity factor of the cable at the operating frequency of 918 MHz As is illustrated in FIG. 5, a hardware-based power divider 111 is utilized in signaling more than one microstrip antennae 104, for example, here four microstrip RF antennas 104. The connector 103 can be configured as a multi-port, coaxial-cable-based divider 111 adapted to distribute evenly the RF power supplied by the RF signal generator to each microstrip antennae 104 through the coaxial feed line, specifically, center conductor 126 and outer conductor 127. It is to be appreciated by those skilled in the art that the method of power division and distribution to microstrip antennas 104 in an array should not limit the scope of the present invention. For example, an alternate and certainly suitable option is a hardware-based power divider 111 adapted to distribute evenly the RF power is a four-way Wilkinson power divider manufactured by MECA Electronics Inc., having model number M4S-1.500W. Another option of many is the four-way reactive power splitter manufactured by CommScope, Inc., having model number Andrew S-4-CPUSE-H-N.

Figure 6:
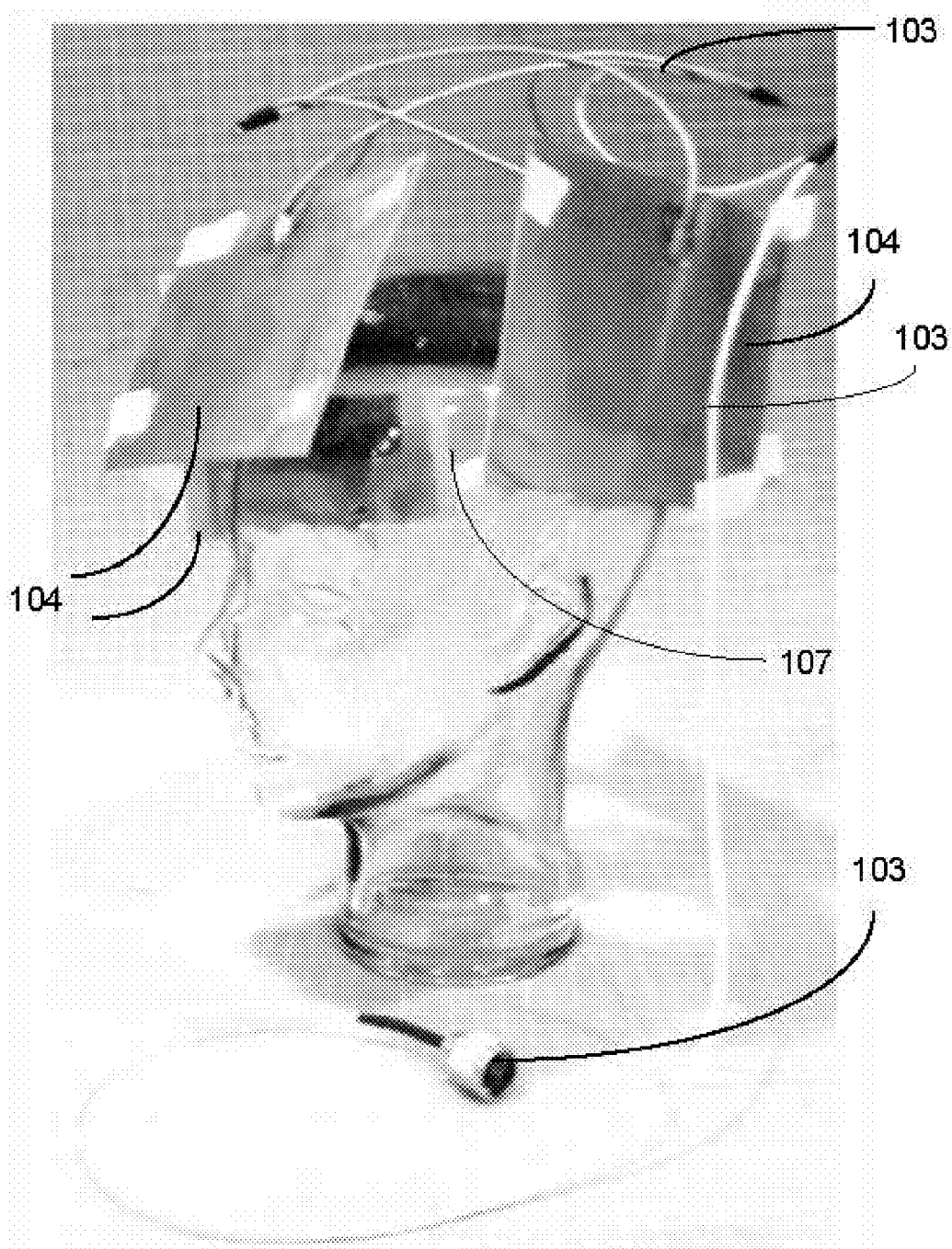
FIG. 6 illustrates a diagram of an embodiment of apparatus, system, and method of the present invention.

As shown in FIG. 6, the four microstrip RF antennas 104 can be arranged in quadrants of the patient's head 106, each microstrip RF antennae 104 being connected to the controller 101, RF signal generator 102 and connectors 103 as is shown in FIGS. 1, 4 and 6. The four-microstrip-antenna configuration 104 illustrates a substantially symmetrical, near-uniform therapeutic RF field about the patient's head 107. The microstrip antennae 104 can be disposed in a helmet 107 as is shown in FIG. 8.

Figure 7:
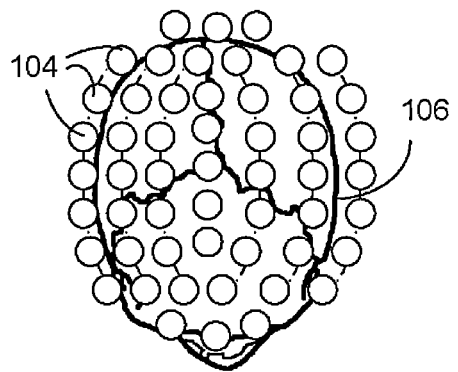
FIG. 7 illustrates a top view of a portable, wearable apparatus incorporating the microstrip RF antenna and a method of treatment according to the present invention.

The selection of four microstrip antennas 104 in this embodiment should not, in any way, limit the scope of the present invention as many other microstrip combinations could be considered—variable in both number and location as are illustrated in FIGS. 7 through 10. For instance, one microstrip antenna 104 can be suitable to provide therapeutic benefits to suppress, prevent or cure according to the method of treatment of the present invention, either stationary or in a pattern, for example, a spiral treatment pattern shown in FIGS. 9 and 10. Alternatively, numerous microstrip antennae 104 can be arranged adjacent to the patient's 106 head, as shown in FIG. 7, or numerous microstrip antennae 104 can be disposed in a helmet 107, as is shown in FIG. 8. With numerous microstrip antennae 104 the system 100 is configured with appropriate signal-splitter technology and required signal-splitter ports (two-port, three-port, four-port, five-port, six-port, etc.) to accommodate the number of microstrip antennas (two, three, four, five, six, etc.) 104. The number of splitters can be selected according to the predetermined number of microstrip antennas 104 used.

Further, the scope of the present invention should not, in any way, be limited by the choice of microstrip antennas in the depicted embodiments. Microstrip antennas represent a compact, efficient antenna design, and hence was the primary choice of the inventor. However, those skilled in the art will recognize that microstrip antennas are just one of a number of antenna types and designs that could suitably function in the present invention. For instance, suitable and operable antenna choices for the present invention include—but not limited to—a dipole antenna, a loop antenna, and a monopole antenna with a ground plane.

According to the principals of the method of treatment of the present invention, therapeutic RF frequencies to suppress, prevent or cure conditions of Alzheimer's and dementia symptoms include those frequencies between approximately 100 kHz and 300 GHz in non-ionizing RF frequency and intensity combination. The present invention uses the frequency of 918 MHz frequency and an intensity or "dosage" of 0.25 watts per kilogram of brain matter. However, as can be appreciated by one skilled in the art an infinite number of frequency and RF dosage combinations are possible and should not, in any way, limit the scope of the present invention with many other frequency and dosage combinations achieving satisfactory results. An unlimited number of frequency and RF-dosage combinations are easily achievable by the present invention by simply adjusting the size and configuration of the microstrip antennas, the frequency and RF output of the RF signal generator, and the configuration of the power divider-amongst other configurable elements.

In another embodiment, the RF field emitted from the RF microstrip antennas 104 utilizes non-symmetrical, non-uniform, and/or intentionally focused patterns via various power-division options.

All of the aforementioned antenna options and configurations should be considered within the intended spirit and scope of the present invention.

It is an object of the present invention to provide a wearable, portable apparatus for the method of treatment which gives clinicians and professionals using the system 100 a broad range of usage options—patients wearing the present invention as a helmet 107 or patients in close-proximity to the present invention—and allows for maximum treatment effectiveness for a wide range of individuals and situations. In an alternative embodiment, the system 100 is incorporated in another structure or element that is in close proximity to the patient such as, for example, apparatus can be affixed to the headboard of a patient's 106 bed, in the mattress under a patient's 106 head, or in the pillow of the patient 106 such as, for example, providing the method of treatment to a patient during rest time or while sleeping.

In operation, according to a method of the present invention (1) one or more microstrip antennas 104 is placed adjacent or on a patient's 106 head; (2) the appropriate RF frequency and intensity dosage is selected on the RF signal generator; and (3) the RF signal generator is turned on. The required time the present invention would remain in the active state would be determined by the clinician, patient parameters, or a predetermined program without causing brain-tissue ionization or any adverse affects.

In an alternative embodiment, a treatment method can be implemented in a software program, whereby the controller 101 is a computer that operates the RF signal generator 102 to apply signals via the connector 103 to the one or more antennae 104 to create a basic non-ionizing RF radiation pattern adjacent or on the patient's 106 head. As above, the controller 101 may be a computer system that is programmed to operate according to a predetermined method of treatment, instructing the RF signal generator 102 and microstrip antennae 103 arranged as an array, network or otherwise used for RF stimulation. The controller 101 is connected to a computer-readable storage medium that can store computer-executable process steps for implementing a method of treatment according to predetermined parameters and patterns.

The computer-executable process steps can comprise a computer program that implements a method of treatment according to predetermined parameters and patterns of the present invention. A predetermined method of treatment can be a basic RF pattern of a substantially symmetrical, near-uniform therapeutic RF field applied adjacent to or on the patient's 106 head so as to stimulate the neurons of the patient 106. As neurons are arranged at every conceivable angle, the predetermined method of treatment can be by other predetermined patterns adapted to provide 360 degree coverage such as, for example, sequentially energizing microstrip antennae 104 to create a spiral therapeutic pattern 115 shown in FIGS. 9 and 10, or by energizing individual antennae 104 shown in FIGS. 7 and 8 in a predetermined pattern. The predetermined patterns are accomplished, in part, by the arrangement of antenna 104 in a network or array. For example, the antennae array or network 104 can be mounted in a predetermined pattern in a helmet 107 (FIG. 8), or otherwise adjacent the patient's 106 head as is shown in FIGS. 7-10. Constant-carrier RF signals or pulsed or modulated (amplitude or frequency) RF signals can be used to stimulate the patient's 106 neurons according to the method of treatment of the present invention. As a result, the present invention is equally capable of constant-carrier, pulsed, and modulated RF signals in various operating modes and these are within the spirit and scope of the present invention.

The method of treatment can be stored in a digital storage medium. The basic RF pattern is derived from a first set of utility functions, each utility function of the first set pertaining to a distinct attribute of a substantially symmetrical, near-uniform therapeutic RF field irradiating the patient's head 106. In this manner, the time and duration of the method of treatment can be controlled by the computer to avoid adverse affects of ionization according to an embodiment of the present invention. For example, a patient 106 can be provided a predetermined number of exposures per day at 918 MHz.

Another predetermined treatment pattern for the method of treatment can be stored in a digital storage medium. The pattern is derived from a set of utility functions to provide 360 degree coverage such as, for example, a spiral pattern 115 shown in FIGS. 9 and 10, or by energizing individual, antennae 104, multiple antennae 104, or both, shown in FIGS. 7 and 8 in a predetermined sequential pattern. As above, the predetermined treatment patterns are accomplished, in part, by the arrangement of antenna 104 in a network or array. For example, the antennae array or network 104 can be mounted in a predetermined arrangement in a helmet 107 (FIG. 8), or otherwise adjacent the patient's 106 head as is shown in FIGS. 7-10.

Figure 11:
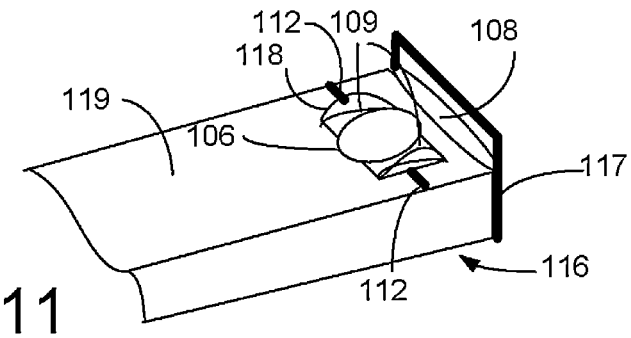
FIG. 11 illustrates a schematic view of treatment according the present invention.

As is shown in FIG. 11, an alternative embodiment of the present invention is described incorporated in another structure or element that is in close proximity to the user rather than being worn by the user. For instance, because of the varied ambulatory nature of patients with Alzheimer's disease, the device 100 could be an antenna bed unit 108 affixed to the headboard 117 of a patient's bed 116, a mattress unit 112 adapted to the mattress 119 under a patient's head 106, or pillow unit 109 in the pillow 118 positioned adjacent the patient's head 106 that the patient is sleeping on. In this embodiment approach, the method of treatment according to the present invention can be achieved in a patient during rest time or while sleeping.

While certain configurations of structures have been illustrated for the purposes of presenting the basic structures of the present invention, one of ordinary skill in the art will appreciate that other variations are possible which would still fall within the scope of the appended claims. For example, polarization techniques can be utilized to vary the relative magnitude and phasing of the antenna system and its elements. By changing the vector orientation and intensity of the applied RF field and how that orientation varies in time, the polarization or polarizations can be tailored to specific methods of treatment of the present invention. A directive radiation pattern can be configured to a single main lobe and several smaller side lobes for specifically targeted brain-tissue density and stimulation of the neurons of the patient. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A portable, wearable, proximal, radio-frequency based system for the treatment of Alzheimer's disease, dementia, and other memory-loss disorders of a brain of a patient, comprising:
   (a) a microstrip antenna unit configured to transmit a signal of radio-frequency (RF) energy in a directional transmission pattern in close proximity to a patient's head,
   (b) said microstrip antenna unit optimized for the radio-frequency selected for medical treatment, said RF energy for said medical treatment is focused at about 1 MHz to 2.5 GHz at an intensity insufficient to ionize molecules of the brain, and (c) said microstrip antenna unit connected to a radio-frequency generator through a radio-frequency transmission line.

2. The system of claim 1 wherein said radio-frequency generator is adapted to deliver appropriate RF energy intensity at said radio frequency selected for medical treatment.

3. The system of claim 1 wherein said radio-frequency generator is constructed to deliver appropriate RF energy intensity at said radio frequency selected for medical treatment.

4. The system of claim 1 wherein said microstrip antenna unit is a plurality of microstrip antennae connected to achieve a directional radio frequency (RF) transmission pattern in close proximity to a patient's head.

5. The system of claim 4 wherein said plurality of microstrip antennae are electrically connected together via a radio-frequency power divider.

6. The system of claim 5 wherein said radio-frequency power divider is a wire-based power divider.

7. The system of claim 6 wherein said wire-based power divider is a phasing-harness-based power divider.

8. The system of claim 6 wherein said wire-based power divider in which the divider wires are wavelength-based cables.

9. The system of claim 6 wherein said wire-based power divider is a Wilkinson wire-constructed power divider.

10. The system of claim 6 wherein said wire-based power divider is a reactive power divider.

11. The system of claim 5 wherein said radio-frequency power divider is a hardware-based power divider.

12. The system of claim 11 wherein said hardware-based power divider is Wilkinson power divider.

13. The system of claim 11 wherein said hardware-based power divider is a reactive power divider.

14. A method for applying radio-frequency stimulation to the brain to treat Alzheimer's disease, dementia, and other memory-loss disorders in a patient, the method comprising:
positioning at least one microstrip antenna device spaced apart of predetermined brain regions of the patient's brain selected for treatment, said positioning locating said at least one microstrip antenna device within approximately up to 30 centimeters distance of said predetermined brain regions, said positioning locating said at least one microstrip antenna device proximate to at least one of said patient's brain regions selected for treatment; and
activating the at least one microstrip antenna device to apply a radio-frequency (RF) signal to at least one of the brain regions in a frequency of about 1 MHz-2.5 GHz and a predetermined intensity in the range of from about approximately between 100 milliwatts to 10 watts insufficient to ionize atoms or molecules of the brain.

15. The method of claim 14 wherein activation of the at least one microstrip antenna unit is applied to treat Alzheimer's disease, dementia, and other memory-loss disorders in a patient.

16. The method of claim 14 wherein a product produced by the method for treating Alzheimer's disease, dementia, and other memory-loss disorders of claim 14.

17. A method for applying radio-frequency stimulation to the brain to treat Alzheimer's disease, dementia, and other memory-loss disorders in a patient, the method comprising:
positioning at least one microstrip antenna device spaced apart of predetermined brain regions of the patient's brain selected for treatment, said positioning locating said at least one antenna device within approximately up to 30 centimeters distance of said predetermined brain regions, said positioning locating said at least one antenna device proximate to at least one of said patient's brain regions selected for treatment; and
activating the at least one microstrip antenna unit to apply a radio-frequency (RF) signal to at least one of one of the brain regions in a frequency in the range of from about between 1 MHz to 2.5 GHz and a predetermined intensity insufficient to ionize atoms or molecules of the brain.

18. The method of claim 17 wherein the step of activating at least one microstrip antenna unit comprises adjusting the RF signal in frequency, pulse width, modulation, or intensity.

19. The method of claim 17 wherein the activating step comprises changing relative magnitude, location, phasing, or polarization of said microstrip antenna unit to modify the EMF pattern emitted.

20. The method of claim 19 wherein the activating step comprises using the at least one antenna unit to apply an RF signal with said predetermined intensity in the range of from about between 100 milliwatts to 10 watts, and said frequency range of from about between 1 MHz to 2.5 GHz.

21. The method of claim 19 wherein the activating step comprises using at least one microstrip antenna unit to apply said RF frequency of 918 MHz and RF dosage of 0.25 watts per brain-matter kilogram.

22. The method of claim 19 wherein the activating step comprises using at least one microstrip antenna unit to apply a pulse width in the range of about between 10 nanoseconds to 500 microseconds.

23. The method of claim 19 wherein the activating step comprises using at least one microstrip antenna unit to apply a constant RF signal for up to hours at a time.

24. The method of claim 19 wherein the activating step comprises modifying the overall RF emission pattern by varying the orientation of at least one microstrip antenna unit.

25. The method of claim 24 whereby the said overall RF emission pattern is a pre-determined pattern around the patient's head.

26. The method of claim 24 whereby the said overall RF emission pattern is a spiral pattern around the patient's head.

27. The method of claim 19 wherein the activating step comprises modifying the overall RF emission pattern by varying the activation sequence of more than one antenna unit.

28. The method of claim 27 wherein said overall RF emission pattern is a pre-determined pattern around the patient's head.

29. The method of claim 27 wherein said overall RF emission pattern is a spiral pattern around the patient's head.

30. The method of claim 19 wherein the activating step comprises activating at least one element of a multi-polar microstrip antenna unit.

31. A non-transitory computer readable storage media having computer-executable instructions, when executed by a processor, performing a method for applying radio-frequency stimulation of the brain to treat Alzheimer's disease, dementia, and other memory-loss disorders in a patient, the method using a computer comprising a CPU, a memory operatively connected to the CPU, and a program stored in the memory and executable by the CPU, the instructions comprising:
in a first computer process, applying a (RF) signal with an intensity in the range of from about between 100 milliwatts to 10 watts, and a frequency of about 1 MHz to 2.5 GHz to at least one microstrip antenna unit; and in a second computer process, varying the RF signal depending on the patient's response to said step of applying the RF signal.

32. The method recited in claim 31, wherein said step of varying the RF signal includes the step of varying the intensity of the RF signal.

33. The method recited in claim 31, wherein said step of varying the RF signal includes the step of varying the duration of time the RF signal is applied.

34. The method recited in claim 31, wherein said step of varying the RF signal includes the step of varying the frequency of the RF signal.

35. The method recited in claim 31, wherein said step of varying the RF signal includes the step of varying the modulation of the RF signal.

36. The method recited in claim 31, wherein said step of applying said RF signal to at least one microstrip antenna unit includes retrieving first pattern for irradiation from a first digital storage medium, the first pattern derived from a first set of utility functions, each utility function of the first set pertaining to a distinct attribute of substantially symmetrical, near-uniform therapeutic RF field about the patient's head.

37. A delivery device for delivering radio-frequency (RF) signals to neurons of the human brain, the device comprising:
   a controller;
   an RF signal generator;
   at least one microstrip antenna unit configured to apply an RF signal at a frequency of between about 1 MHz to 2.5 GHz;
   a connector for transmitting power from said RF signal generator to the at least one microstrip antenna unit under the control of said control system; and
   characterized by said control system activating at least one microstrip antenna unit to apply said RF signal at said frequency to at least one of one of the brain nerve cells in a predetermined dosage of approximately 0.25 watts per brain-matter kilogram insufficient to ionize atoms or molecules of the brain nerve cells.

38. A delivery device of claim 37 wherein said at least one microstrip antenna unit is positioned spaced apart of predetermined brain regions of the patient's brain selected for treatment, said positioning locating said at least one microstrip antenna device within approximately up to 30 centimeters distance of said predetermined brain regions, said positioning locating said at least one antenna device proximate to at least one of the patient's brain nerve cells in said patient's brain regions selected for treatment. (Dec. Knight ¶¶30-32).

39. A delivery device of claim 37 wherein said at least one microstrip antenna unit is positioned inside a helmet, the helmet can be placed on the patient's head so as to arrange at least one of said microstrip antenna unit spaced apart of predetermined brain regions of the patient's brain selected for treatment, said positioning locating said at least one antenna device within approximately up to 30 centimeters distance of said predetermined brain regions, said positioning locating said at least one microstrip antenna device proximate to the patient's brain nerve cells in said patient's brain regions selected for treatment. (Dec. Knight ¶¶30-32).

* * * * *